United States Patent
Munsinger et al.

(10) Patent No.: US 10,058,443 B2
(45) Date of Patent: Aug. 28, 2018

(54) STENT DELIVERY SYSTEMS AND METHODS FOR USE

(71) Applicant: BOSTON SCIENTIFIC SCIMED, INC., Maple Grove, MN (US)

(72) Inventors: Joel R. Munsinger, Blaine, MN (US); Gary J. Pederson, Jr., Albertville, MN (US); Michael D. Gerdts, Big Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 513 days.

(21) Appl. No.: 13/666,547

(22) Filed: Nov. 1, 2012

(65) Prior Publication Data
US 2013/0110223 A1   May 2, 2013

Related U.S. Application Data

(60) Provisional application No. 61/554,803, filed on Nov. 2, 2011.

(51) Int. Cl.
*A61F 2/966* (2013.01)
*A61F 2/95* (2013.01)

(52) U.S. Cl.
CPC ...... *A61F 2/966* (2013.01); *A61F 2002/9517* (2013.01); *A61F 2250/0029* (2013.01)

(58) Field of Classification Search
CPC .................................. A61F 2/95–2/97; A61F 2002/9505–2002/9665
USPC ................. 606/1, 108; 623/1.11–1.125, 1.23
See application file for complete search history.

(56) References Cited

U.S. PATENT DOCUMENTS

| | | | |
|---|---|---|---|
| 3,613,684 A | 10/1971 | Sheridan |
| 4,665,918 A | 5/1987 | Garza et al. |
| 4,732,152 A | 3/1988 | Wallsten et al. |
| 4,906,232 A | 3/1990 | Reynolds |
| 5,026,377 A | 6/1991 | Burton et al. |
| 5,071,407 A | 12/1991 | Termin et al. |
| 5,158,548 A | 10/1992 | Lau et al. |
| 5,163,905 A | 11/1992 | Don Michael |
| 5,201,757 A | 4/1993 | Heyn et al. |
| 5,221,261 A | 6/1993 | Termin et al. |
| 5,238,004 A | 8/1993 | Sahatjian et al. |
| 5,346,471 A | 9/1994 | Raulerson |
| 5,378,239 A | 1/1995 | Termin et al. |
| 5,433,723 A | 7/1995 | Lindenberg et al. |
| 5,443,907 A | 8/1995 | Slaikeu et al. |
| 5,445,646 A | 8/1995 | Euteneuer et al. |

(Continued)

OTHER PUBLICATIONS

International Search Report for Corresponding Application No. PCT/US2012/063043, dated Jan. 11, 2012.

*Primary Examiner* — Darwin Erezo
*Assistant Examiner* — Jonathan Hollm
(74) *Attorney, Agent, or Firm* — Seager, Tufte & Wickhem LLP

(57) ABSTRACT

The disclosure describes stent delivery systems and its related methods of use. A stent delivery system including an inner shaft with a stent disposed about the distal region, a deployment sheath slidably disposed about the inner shaft, a handle coupled to the deployment sheath, and an intermediate shaft disposed about the inner shaft, positioned proximally of the stent. Further, proximal portion of the intermediate shaft is disposed within the handle and includes a support member.

20 Claims, 10 Drawing Sheets

(56) References Cited

U.S. PATENT DOCUMENTS

| | | | |
|---|---|---|---|
| 5,496,277 A | 3/1996 | Termin et al. |
| 5,534,007 A | 7/1996 | St. Germain et al. |
| 5,571,135 A | 11/1996 | Fraser et al. |
| 5,662,703 A | 9/1997 | Yurek et al. |
| 5,674,242 A | 10/1997 | Phan et al. |
| 5,690,644 A | 11/1997 | Yurek et al. |
| 5,695,499 A | 12/1997 | Helgerson et al. |
| 5,702,364 A | 12/1997 | Euteneuer et al. |
| 5,713,860 A | 2/1998 | Kaplan et al. |
| 5,733,267 A | 3/1998 | Del Toro |
| 5,755,777 A | 5/1998 | Chuter |
| 5,772,609 A | 6/1998 | Nguyen et al. |
| 5,772,669 A | 6/1998 | Vrba |
| 5,788,707 A | 8/1998 | Del Toro et al. |
| 5,827,242 A | 10/1998 | Follmer et al. |
| 5,830,181 A | 11/1998 | Thornton |
| 5,833,694 A | 11/1998 | Poncet |
| 5,833,706 A | 11/1998 | St. Germain et al. |
| 5,843,090 A | 12/1998 | Schuetz |
| 5,843,091 A | 12/1998 | Holsinger |
| 5,882,347 A | 3/1999 | Mouris-Laan et al. |
| 5,891,154 A | 4/1999 | Loeffler |
| 5,906,619 A | 5/1999 | Olson et al. |
| 5,954,764 A | 9/1999 | Parodi |
| 5,957,930 A | 9/1999 | Vrba |
| 5,980,483 A | 11/1999 | Dimitri |
| 5,997,562 A * | 12/1999 | Zadno-Azizi et al. ........ 606/194 |
| 6,017,577 A | 1/2000 | Hostettler et al. |
| 6,019,778 A | 2/2000 | Wilson et al. |
| 6,033,413 A | 3/2000 | Mikus et al. |
| 6,059,813 A | 5/2000 | Vrba et al. |
| 6,117,140 A | 9/2000 | Munsinger |
| 6,120,522 A | 9/2000 | Vrba et al. |
| 6,123,723 A | 9/2000 | Konya et al. |
| 6,139,510 A | 10/2000 | Palermo |
| 6,139,524 A | 10/2000 | Killion |
| 6,159,228 A * | 12/2000 | Frid ............... A61F 2/95 606/108 |
| 6,176,849 B1 | 1/2001 | Yang et al. |
| 6,190,393 B1 * | 2/2001 | Bevier ............ A61F 2/958 604/96.01 |
| 6,206,888 B1 | 3/2001 | Bicek et al. |
| 6,221,467 B1 | 4/2001 | Nazarova et al. |
| 6,238,410 B1 | 5/2001 | Vrba et al. |
| 6,254,609 B1 | 7/2001 | Vrba et al. |
| 6,287,329 B1 | 9/2001 | Duerig et al. |
| 6,322,586 B1 | 11/2001 | Monroe et al. |
| 6,330,884 B1 | 12/2001 | Kim |
| 6,331,184 B1 | 12/2001 | Abrams |
| 6,342,066 B1 | 1/2002 | Toro et al. |
| 6,355,060 B1 | 3/2002 | Lenker et al. |
| 6,375,676 B1 | 4/2002 | Cox |
| 6,379,365 B1 | 4/2002 | Diaz |
| 6,380,457 B1 | 4/2002 | Yurek et al. |
| 6,391,050 B1 | 5/2002 | Broome |
| 6,398,802 B1 | 6/2002 | Yee |
| 6,402,760 B1 * | 6/2002 | Fedida ............ A61F 2/95 604/528 |
| 6,425,898 B1 | 7/2002 | Wilson et al. |
| 6,508,803 B1 | 1/2003 | Horikawa et al. |
| 6,514,228 B1 | 2/2003 | Hamilton et al. |
| 6,514,261 B1 | 2/2003 | Randall et al. |
| 6,544,278 B1 | 4/2003 | Vrba et al. |
| 6,576,006 B2 | 6/2003 | Limon et al. |
| 6,589,251 B2 | 7/2003 | Yee et al. |
| 6,602,226 B1 | 8/2003 | Smith et al. |
| 6,613,014 B1 | 9/2003 | Chi |
| 6,626,934 B2 | 9/2003 | Blaeser et al. |
| 6,669,716 B1 | 12/2003 | Gilson et al. |
| 6,726,712 B1 | 4/2004 | Raeder-Devens et al. |
| 6,726,714 B2 | 4/2004 | DiCaprio et al. |
| 6,736,839 B2 | 5/2004 | Cummings |
| 6,755,855 B2 | 6/2004 | Yurek et al. |
| 6,773,446 B1 | 8/2004 | Dwyer et al. |
| 6,776,791 B1 | 8/2004 | Stallings et al. |
| 6,802,849 B2 | 10/2004 | Blaeser et al. |
| 6,860,898 B2 | 3/2005 | Stack et al. |
| 6,939,352 B2 | 9/2005 | Buzzard et al. |
| 6,942,682 B2 | 9/2005 | Vrba et al. |
| 6,951,675 B2 | 10/2005 | Chin et al. |
| 7,001,423 B2 | 2/2006 | Euteneuer et al. |
| 7,387,640 B2 | 6/2008 | Cummings |
| 7,632,296 B2 | 12/2009 | Malewicz |
| 7,740,652 B2 | 6/2010 | Gerdts et al. |
| 8,128,676 B2 | 3/2012 | Cummings |
| 8,152,818 B2 | 4/2012 | Gunderson |
| 2001/0034548 A1 | 10/2001 | Vrba et al. |
| 2001/0034549 A1 * | 10/2001 | Bartholf ............ A61F 2/95 623/1.12 |
| 2001/0037141 A1 | 11/2001 | Yee et al. |
| 2002/0052641 A1 | 5/2002 | Monroe et al. |
| 2002/0058951 A1 | 5/2002 | Fielder |
| 2002/0082550 A1 | 6/2002 | Hamilton et al. |
| 2002/0095203 A1 * | 7/2002 | Thompson .......... A61F 2/95 623/1.11 |
| 2002/0103525 A1 | 8/2002 | Cummings |
| 2002/0165523 A1 | 11/2002 | Chin et al. |
| 2003/0163156 A1 | 8/2003 | Hebert et al. |
| 2004/0098083 A1 | 5/2004 | Tran et al. |
| 2004/0148007 A1 * | 7/2004 | Jackson ............ A61F 2/95 623/1.12 |
| 2004/0148009 A1 | 7/2004 | Buzzard et al. |
| 2004/0215317 A1 | 10/2004 | Cummings |
| 2004/0267348 A1 | 12/2004 | Gunderson et al. |
| 2005/0027306 A1 * | 2/2005 | Krivoruchko et al. ....... 606/108 |
| 2005/0027345 A1 * | 2/2005 | Horan et al. ................. 623/1.12 |
| 2005/0080476 A1 | 4/2005 | Gunderson et al. |
| 2005/0090890 A1 * | 4/2005 | Wu .................. A61F 2/95 623/1.11 |
| 2005/0149159 A1 | 7/2005 | Andreas et al. |
| 2005/0154439 A1 | 7/2005 | Gunderson |
| 2005/0182475 A1 | 8/2005 | Jen et al. |
| 2005/0192657 A1 | 9/2005 | Arai et al. |
| 2005/0240254 A1 | 10/2005 | Austin |
| 2005/0256562 A1 | 11/2005 | Cierc et al. |
| 2006/0009833 A1 | 1/2006 | Chobotov et al. |
| 2006/0030923 A1 | 2/2006 | Gunderson |
| 2006/0041302 A1 | 2/2006 | Malewicz |
| 2006/0074477 A1 | 4/2006 | Berthiaume et al. |
| 2006/0100687 A1 * | 5/2006 | Fahey ............... A61F 2/95 623/1.11 |
| 2006/0190069 A1 | 8/2006 | Baker-Janis et al. |
| 2006/0229697 A1 | 10/2006 | Gerdts et al. |
| 2006/0292300 A1 | 12/2006 | Tan |
| 2007/0118201 A1 * | 5/2007 | Pappas ............. A61F 2/95 623/1.11 |
| 2007/0142894 A1 | 6/2007 | Moore et al. |
| 2007/0208350 A1 | 9/2007 | Gunderson |
| 2007/0282420 A1 | 12/2007 | Gunderson |
| 2007/0293930 A1 * | 12/2007 | Wang et al. .................. 623/1.11 |
| 2008/0097395 A1 * | 4/2008 | Adams ............ A61M 25/0021 604/524 |
| 2008/0097396 A1 * | 4/2008 | Spencer .......... A61M 25/0054 604/525 |
| 2008/0188920 A1 | 8/2008 | Moberg et al. |
| 2009/0036967 A1 | 2/2009 | Cummings |
| 2009/0192518 A1 | 7/2009 | Golden et al. |
| 2009/0192584 A1 * | 7/2009 | Gerdts .............. A61F 2/95 623/1.11 |
| 2009/0264988 A1 | 10/2009 | Mafi et al. |
| 2010/0256727 A1 | 10/2010 | Gerdts et al. |
| 2011/0137401 A1 * | 6/2011 | Dorn ................ A61F 2/95 623/1.12 |
| 2012/0136425 A1 * | 5/2012 | Orr ................... A61F 2/95 623/1.11 |

* cited by examiner

STENT DELIVERY SYSTEMS AND METHODS FOR USE

CROSS-REFERENCE TO RELATED APPLICATIONS

This application claims priority under 35 U.S.C. § 119 to U.S. Provisional Application Ser. No. 61/554,803, filed Nov. 2, 2011, the entirety of which is incorporated herein by reference.

TECHNICAL FIELD

The present invention pertains to medical devices and methods for making and using medical devices. More particularly, the present invention pertains to stent delivery systems.

BACKGROUND

A wide variety of intracorporeal medical devices have been developed for medical use, for example, intravascular use. Some of these devices include stent delivery systems. These devices are manufactured by any one of a variety of different manufacturing methods and may be used according to any one of a variety of methods. Of the known stent delivery devices and methods for making and using the same, each has certain advantages and disadvantages. There is an ongoing need to provide alternative stent delivery devices as well as alternative methods for making and using stent delivery devices.

BRIEF SUMMARY

The invention provides design, material, manufacturing method, and use alternatives for stent delivery systems including self-expanding stent delivery systems. An example stent delivery system may include an inner shaft having a distal region. A stent may be disposed about the distal region. A deployment sheath may be slidably disposed about the inner shaft. A handle may be coupled to the deployment sheath. An intermediate shaft may be disposed about the inner shaft and positioned proximally of the stent. A proximal portion of the intermediate shaft may be disposed within the handle and may include a support member.

Another example stent delivery system may include an inner shaft having a distal region. A stent may be disposed about the distal region. A deployment sheath may be slidably disposed about the inner shaft. A handle may be coupled to the deployment sheath. The handle may include handle housing. An intermediate shaft may be disposed about the inner shaft and positioned proximally of the stent. A supported portion of the intermediate shaft may extend within the handle housing. The supported portion may be configured to resist bowing of the intermediate shaft during proximal retraction of the deployment sheath. An outer shaft may be disposed about the intermediate shaft and positioned proximally of the stent.

An example method for delivering a stent may include providing a stent delivery system. The stent delivery system may include an inner shaft having a distal region, a stent disposed about the distal region, a deployment sheath slidably disposed about the inner shaft, a handle coupled to the deployment sheath, and an intermediate shaft disposed about the inner shaft and positioned proximally of the stent. A proximal portion of the intermediate shaft may be disposed within the handle and may include a support member. The method may also include advancing the stent delivery system through a body lumen to a position adjacent to an area of interest, proximally retracting the deployment sheath, such that the support member may resist bowing of the intermediate shaft during proximal retraction of the deployment sheath.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
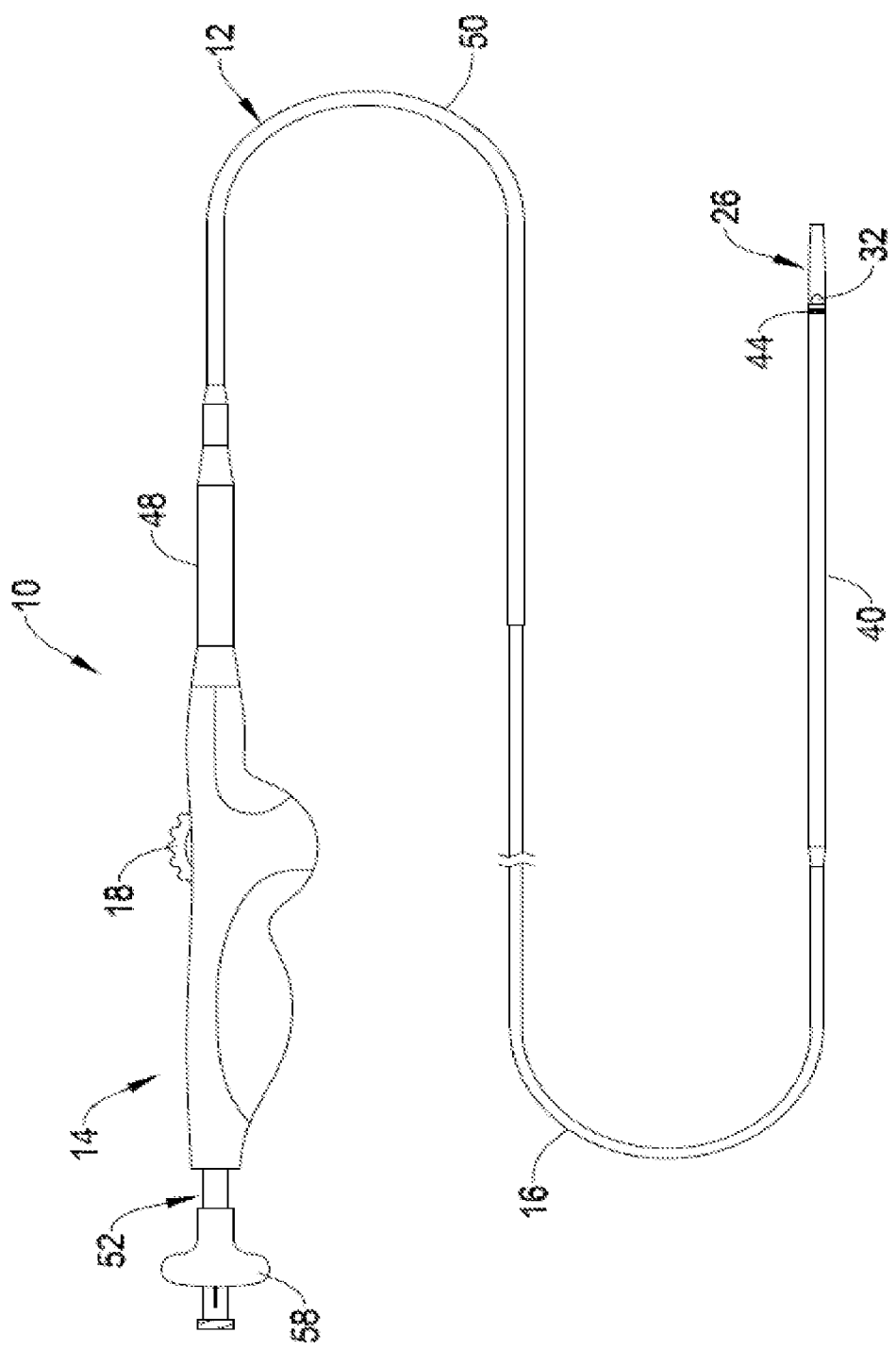
FIG. 1 is a partial cross-sectional side view of an example stent delivery system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 illustrates an example stent delivery system 10. System 10 may include an elongate shaft 12 and a handle 14 coupled to shaft 12. In general, system 10 may be used to deliver a suitable stent, graft, endoprosthesis or the like to an area of interest within a body lumen of a patient. The body lumen may be a blood vessel (e.g., artery or vein) located near the heart (e.g., within or near a cardiac vessel), within a peripheral vessel, within a neurological vessel, or at any other suitable location. Deployment of the stent may include the proximal retraction of a deployment sheath 16, which overlies the stent. Refraction of deployment sheath 16 may include the actuation of an actuation member 18 generally disposed at handle 14. In the example illustrated in FIG. 1, actuation member 18 is a thumb wheel that can be rotated by a clinician in order to accomplish proximal retraction of deployment sheath 16. Numerous other actuation members are contemplated. A number of other structures and features of system 10 can be seen in FIG. 1 and are labeled with reference numbers. Additional discussion of these structures can be found below.

Figure 2:
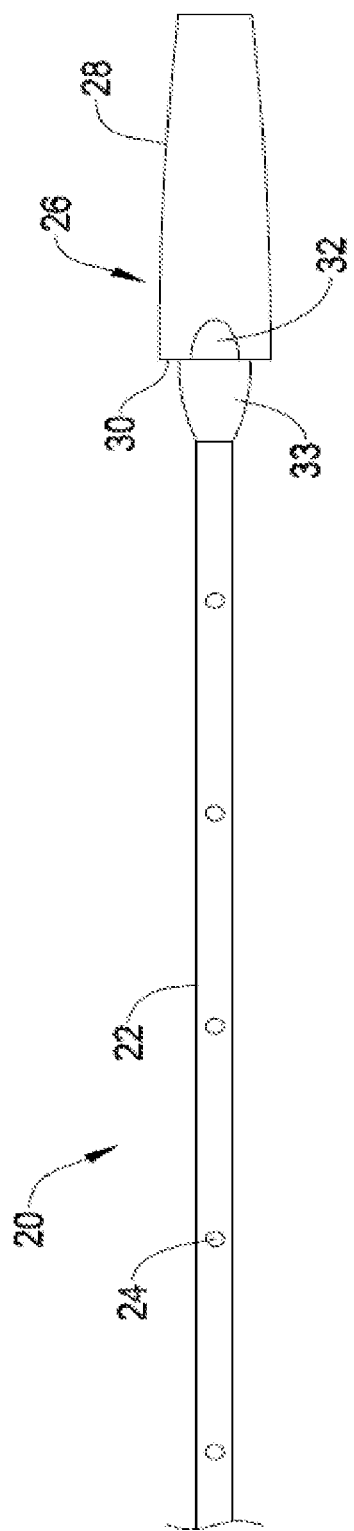
FIG. 2 is a side view of a portion of the example stent delivery system shown in FIG. 1.

FIGS. 2-6 illustrate at least some of the structural components that may be included as a part of system 10. For example, system 10 may include an inner shaft or member 20 as illustrated in FIG. 2. In at least some embodiments, inner member 20 may be a tubular structure and, thus, may include a lumen (not shown). The lumen may be a guidewire lumen that extends along at least a portion of the length of inner member 20. Accordingly, system 10 may be advanced over a guidewire to the desired target location in the vasculature. In addition, or in alternative embodiments, the lumen may be a perfusion/aspiration lumen that allows portions, components, or all of system 10 to be flushed, perfused, aspirated, or the like.

Inner member 20 may include a stent receiving region 22 about which a stent (not shown, can be seen in FIGS. 3-4) may be disposed. The length and/or configuration of stent receiving region 22 may vary. For example, stent receiving region 22 may have a length sufficient for the stent to be disposed thereon. It can be appreciated that as the length of the stent utilized for system 10 increases, the length of stent receiving region 22 also increases.

Along or otherwise disposed adjacent stent receiving region 22 may be one or more perfusion ports 24. Ports 24 may extend through the wall of inner member 20 such that fluid may be infused through the lumen of inner member 20 and may be flushed through ports 24. This may be desirable for a number of reasons. For example, ports 24 may allow a clinician to evacuate air bubbles that may be trapped adjacent the stent by perfusing fluid through ports 24. In addition, ports 24 may be used to aspirate fluid that may be disposed along inner member 20. Ports 24 may also aid in sterilization and/or other preparatory processing steps that may be involved in preparing system 10 for sale.

A tip 26 may be attached to or otherwise disposed at the distal end of inner member 20. Tip 26 may generally have a rounded or smooth shape that provides a generally atraumatic distal end to system 10. For example, tip 26 may have a smooth tapered distal portion 28 that gently tapers. Tip may also include a proximal ridge 30 that is configured so that deployment sheath 16 can abut therewith. Tip 26 may also include a tapered proximal portion 33. Numerous other shapes and/or configurations are contemplated for tip 26.

Tip 26 may also include one or more cutouts or flats 32 formed therein. For the purposes of this disclosure, flats 32 are understood to be cutouts or flattened portions of tip 26 where the outer dimension or profile of tip 26 is reduced. The name "flats" comes from the fact that these regions may have a somewhat "flat" appearance when compared to the remainder of tip 26, which generally may have a rounded profile. The shape, however, of flats 32 is not meant to be limited to being flat or planar as numerous shapes are contemplated.

Flats 32 may allow for a gap or space to be defined between inner member 20 and deployment sheath 16 when deployment sheath 16 abuts proximal ridge 30 of tip 26. This gap may allow for fluid, for example perfusion fluid passed through ports 24, to flow out from deployment sheath 16. Thus, flats 32 may be used in conjunction with ports 24 to allow portions or all of system 10 to be flushed or otherwise evacuated of air bubbles.

Figure 3:
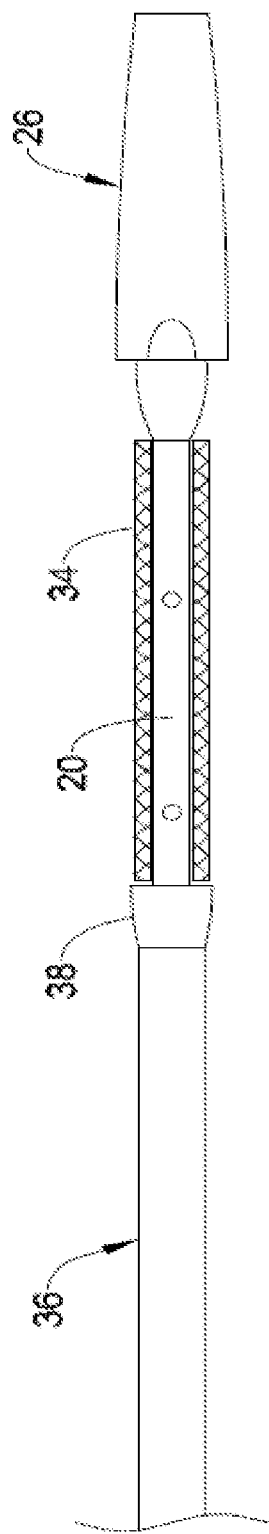
FIG. 3 is a side view of another portion of the example stent delivery system shown in FIG. 1.

FIG. 3 illustrates inner member 20 with some additional structure of system 10. In this figure, a stent 34 is disposed about inner member 20 (e.g., about stent receiving region 22 of inner member 20). In some embodiments, stent 34 is a self-expanding stent. Accordingly, stent 34 may be biased to outwardly expand. Because of this, stent 34 may not be "loaded onto" inner member 20 in a strict sense but rather may be thought of as being disposed about or surrounding inner member 20. Stent 34 may then be restrained within deployment sheath 16. In alternative embodiments, however, stent 34 may be directly loaded onto inner member 20 via crimping or any other suitable mechanical holding mechanism.

An intermediate tube 36 may also be disposed over inner member 20. In at least some embodiments, intermediate tube 36 may extend from a position adjacent to the proximal end of inner member 20 to a position proximal of the distal end of inner member 20. Intermediate tube 36 may include a bumper 38. In practice, bumper 38 may function by preventing any unwanted proximal movement of stent 34 during navigation and/or deployment of stent 34.

Bumper 38 may have any suitable form. In some embodiments, bumper 38 may be defined by a relatively short tube or sleeve that is disposed about intermediate tube 36. The material utilized for the sleeve may be the same or different from that of intermediate tube 36. Intermediate tube 36 may have a tapered or otherwise smooth transition in outer diameter adjacent bumper 38. For example, polymeric material may be disposed or reflowed adjacent bumper 38 (which may include disposing the polymeric material about a portion or all of bumper 38) so as to define a gentle transition in outer diameter at bumper 38. Other configurations are contemplated and may be utilized in alternative embodiments.

Figure 4:
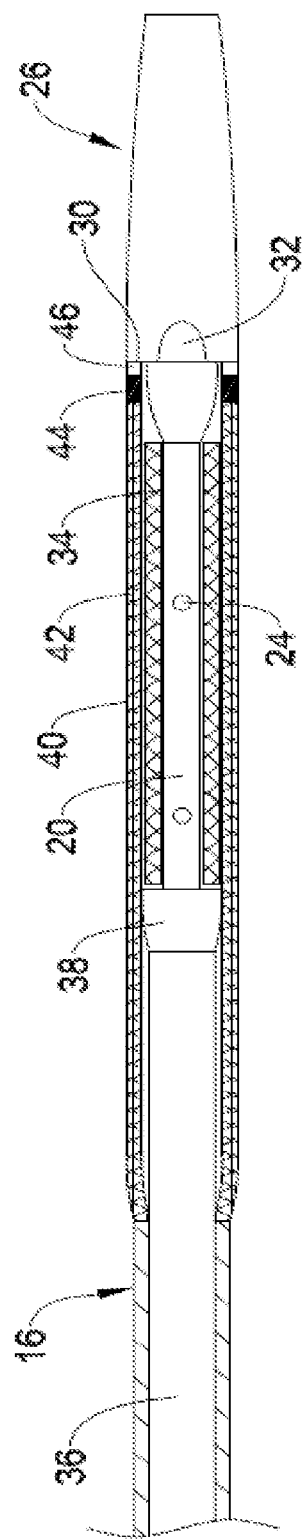
FIG. 4 is a side view of another portion of the example stent delivery system shown in FIG. 1.

FIG. 4 illustrates additional structure of system 10. Here deployment sheath 16 can be seen disposed over inner member 20, intermediate tube 36, and stent 34. It can be appreciated that deployment sheath 16 is configured to shift between a first position, for example as shown in FIG. 4, where deployment sheath 16 overlies stent 34 and a second position where deployment sheath 16 is proximally retracted to a position substantially proximal of stent 34. In general, the first position may be utilized during navigation of system 10 to the appropriate location within a body lumen and the second position may be used to deploy stent 34.

Deployment sheath 16 may include a stepped portion 40 where the outer diameter of deployment sheath 16 is increased. In stepped portion 40, the thickness of the tubular wall of deployment sheath 16 may or may not be increased. Stepped portion 40 may be desirable for a number of reasons. For example, stepped portion 40 may allow deployment sheath 16 to have an adequate inner dimension that is suitable so that deployment sheath 16 may be disposed about stent 34 and bumper 38. In at least some embodiments, stepped portion 40 is positioned at or near the distal end of deployment sheath 16. In addition, the transition in outer diameter between the "non-stepped" portion of deployment sheath 16 and stepped portion 40 may be positioned proximally of stent 34 when deployment sheath 16 is disposed over stent 34.

In at least some embodiments, deployment sheath 16 may include a reinforcing member 42 embedded or otherwise included therewith. Reinforcing member 42 may have any number of a variety of different configurations. For example, reinforcing member 42 may include a braid, coil, mesh, combinations thereof, or the like, or any other suitable configuration. In some embodiments, reinforcing member 42 may extend along the entire length of deployment sheath 16. In other embodiments, reinforcing member 42 may extend along one or more portions of the length of deployment sheath 16. For example, reinforcing member 42 may extend along stepped portion 40.

Deployment sheath 16 may also include a radiopaque marker or band 44. In general, marker band 44 may be disposed adjacent to the distal end 46 of deployment sheath 16. One or more additional marker bands 44 may be disposed along other portions of deployment sheath 16 or other portions of system 10. Marker band 44 may allow the distal end 46 of deployment sheath 16 to be fluoroscopically visualized during advancement of system 10 and/or deployment of stent 34.

FIG. 4 also illustrates the distal end 46 of deployment sheath 16 abutting proximal ridge 30. In this configuration, stent 34 can be flushed (e.g., to remove air bubbles) by infusing fluid through inner member 20 and through ports 24. Because of flats 32, fluid may be allowed to be flushed out of deployment sheath 16 by passing through the gaps formed between inner member 20 and deployment sheath 16 at flats 32.

Figure 5:
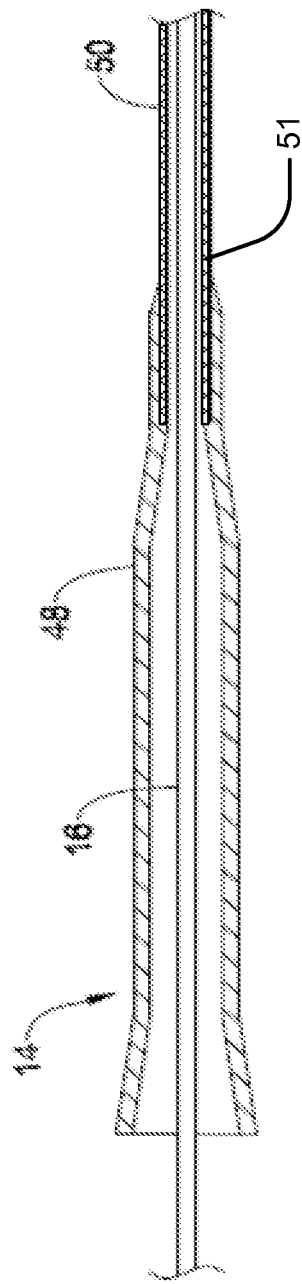
FIG. 5 is a side view of another portion of the example stent delivery system shown in FIG. 1.

FIG. 5 illustrates a distal portion 48 of handle 14. Here it can be seen that handle 14 is attached to an outer member 50. Outer member 50 may be disposed about deployment sheath 16 and extend along a portion of the length of deployment sheath 16. Thus, along at least a portion of the length of system 10, system 10 may include four tubular structures that may be coaxially arranged—namely outer member 50, deployment sheath 16, intermediate tube 36, and inner member 20. In at least some embodiments, outer member 50 may provide system 10 with a number of desirable benefits. For example, outer member 50 may include or otherwise be formed from a lubricious material that can reduce friction that may be associated with proximally retracting deployment sheath 16. In addition, outer member 50 may comprise a surface that can be clamped or otherwise locked so that the position of system 10 can be maintained without negatively impacting the retraction of deployment sheath 16 (which might otherwise be impacted if deployment sheath 16 was to be clamped). Furthermore, outer member 50 may include a reinforcement 51. The form and/or configuration of reinforcement 51 may vary. For example, in at least some embodiments, reinforcement 51 may take the form of a braid. Alternatively, reinforcement 51 may be a coil or other reinforcing structure. Reinforcement 51 may include any suitable material including those materials disclosed herein (e.g., metals, polymers, etc.). Numerous other desirable benefits may also be achieved through the use of outer member 50.

Figure 6:
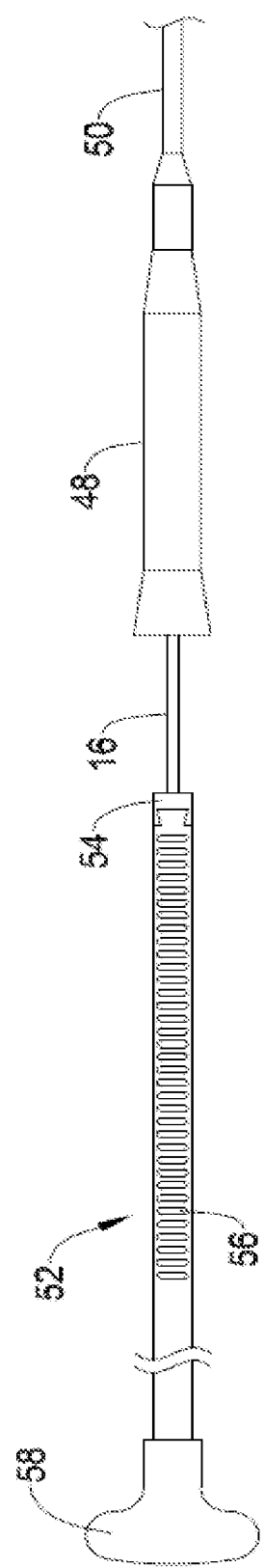
FIG. 6 is a side view of another portion of the example stent delivery system shown in FIG. 1.

Deployment sheath 16 may pass proximally through outer member 50 and extend proximally back within handle 14. Intermediate tube 36 and inner member 20 both also extend back within handle 14 and are disposed within deployment sheath 16. The proximal end of deployment sheath 16 may be attached to a gear rack assembly 52 with a fastener or clip 54 as illustrated in FIG. 6. Thus, it can be appreciated that proximal movement of gear rack assembly 52 may result in analogous proximal movement of deployment sheath 16. Gear rack assembly 52 may include a plurality of teeth or gears 56. In practice, teeth 56 may be configured to engage with corresponding teeth or gears (not shown) on thumbwheel 18. Consequently, rotation of thumbwheel 18, via gearing thereof with gears 56, can be utilized to proximally retract gear rack assembly 52 and, thus, deployment sheath 16. Other structural arrangements may be utilized to accomplish proximal retraction of gear rack assembly 52 through the actuation of thumbwheel 18 or any other suitable actuation member.

Figure 7:
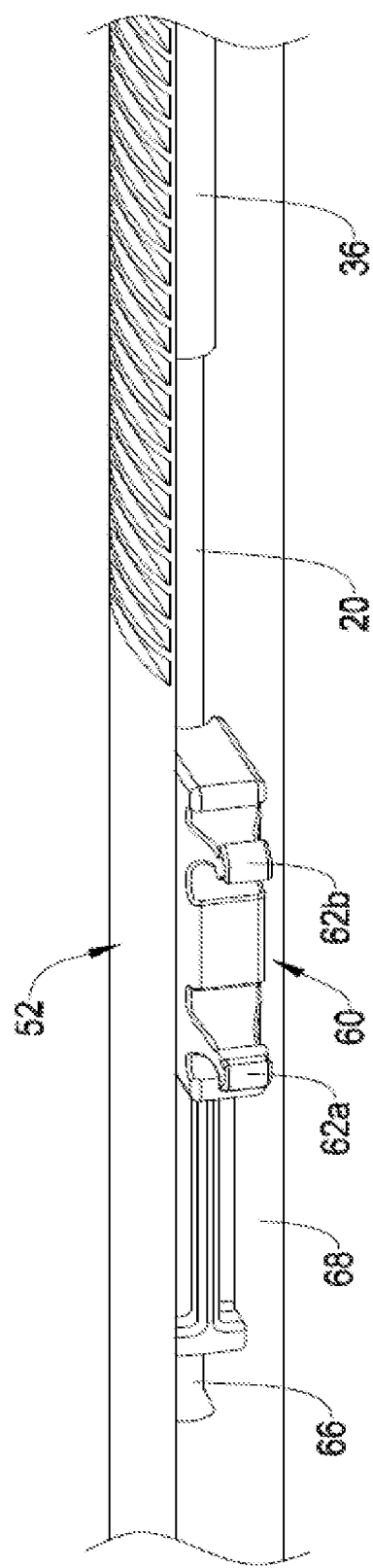
FIG. 7 is a side view of another portion of the example stent delivery system shown in FIG. 1.

Gear rack assembly 52 may also include a flared proximal end 58. When properly assembly, the main body of gear rack assembly 52 may be disposed within handle 14 and proximal end 58 may be disposed along the exterior of handle 14. Gear rack assembly 52 may have a slot or groove 68 formed therein (not shown in FIG. 6, can be seen in FIG. 7). Groove 68 may extend the length of gear rack assembly 52, including extending along proximal end 58. Because proximal end 58 may be generally located near the proximal end of inner member 20, the flared shape of proximal end 58 and the orientation of groove 68 may allow proximal end 58 to function as a guidewire introducer or funnel that may assist a clinician in placing, holding, removing, and/or exchanging a guidewire extending through inner member 20.

In order to properly deploy stent 34, the various components of system 10 need to work in concert so that relative motion of deployment sheath 16 can be accomplished relative to inner member 20. In addition, to improve the accuracy of deployment, intermediate tube 36 needs to be configured so as to provide the desired longitudinal support necessary to limit proximal movement of stent 34. In at least some embodiments, the proper configuration of these structures may be maintained, at least in part, through the use of a clip member 60. In general, clip member 60 is disposed within handle 14 and is configured to be secured along the interior of handle 14. Accordingly, clip member 60 allows the longitudinal position of one or more portions of system 10 to be fixed relative to handle 14. In order to secure clip member 60 to handle 14, clip member 60 may include one or more fasteners or legs 62a/62b. For example, handle 14 may have one or more slots, grooves, openings, or the like that are configured to seat legs 62a/62b such that the relative position of clip member 60 relative to handle 14 is fixed. In some embodiments, clip member 60 may be configured to "snap in" to handle 14. This may desirably simplify manufacturing.

The orientation of clip member 60 may be such that it is positioned near one or more structures of system 10. In at least some embodiments, clip member 60 may be configured so that at least a portion thereof is positioned within groove 68 of gear rack assembly 52. This may desirably place clip member 60 near inner member 20 and intermediate tube 36

(which may also extend through groove 68) such that clip member 60 can be associated therewith.

Inner member 20 may be coupled with clip member 60 such that the longitudinal position of inner member 20 can be fixed relative to handle 14. For example, clip member 60 may include one or more tubular sections, through which inner member 20 may extend therethrough. In some embodiments, a flared proximal end 66 of inner member 20 may extend out proximally from clip member 60. Flared proximal end 66 may substantially prevent any unwanted distal movement of inner member 20. Thus, the longitudinal position (e.g., at least with respect to distal movement of inner member 20) of inner member 20 can be fixed. In other embodiments, the proximal end of clip member 60 may have a constant outer diameter (e.g., the proximal end may not be flared) and the opening formed in clip member 60 may have a flared inner diameter. In these embodiments, the flared opening in clip member 60 may help aid a clinician in guiding a guidewire therein and into inner member 20. A sleeve or cuff (not shown) may also be disposed over inner member 20 and positioned between the tubular sections of clip member 60 to prevent any unwanted proximal and/or distal movement of inner member 20 relative to handle 14.

During deployment of stent 34, a number of forces may be exerted onto various portions of system 10. For example, retraction of deployment sheath 16 may have a tendency to exert a compressive force onto inner shaft 20, intermediate shaft 36, or both. Furthermore, because inner shaft 20 and intermediate shaft 36 may lie within handle 14, compressive forces on these structures could cause them to flex, bend, bow, or kink. System 10 includes one or more structural features that may help reduce the possibility that inner shaft 20, intermediate shaft 36, or both may flex, bend, bow, or kink.

Figure 8:
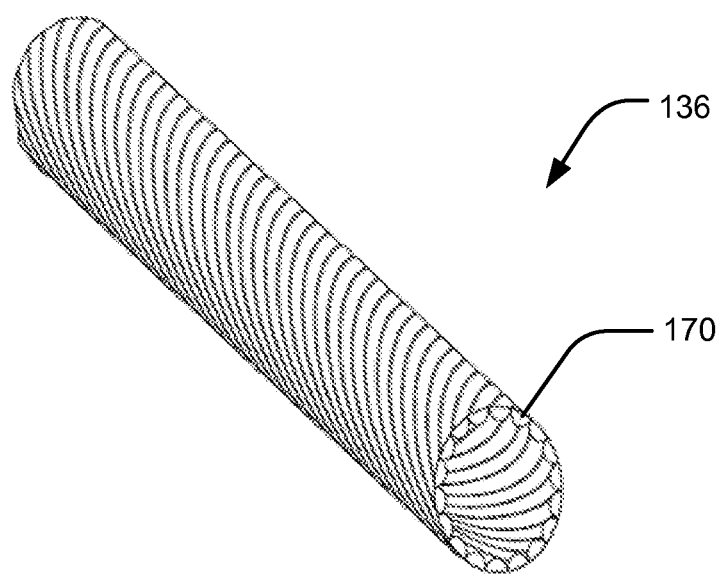
FIG. 8 is a side view of a portion of an example intermediate shaft.

FIG. 8 is a side view of a portion of an example intermediate shaft 136 that may be used with system 10. In general, intermediate shaft 136 may be designed to increase stiffness and kink resistance. In other words, intermediate shaft 136 may be formed from or otherwise include a support structure or member that provide resistance to bending, bowing, kinking, etc. of intermediate shaft 136 and/or inner shaft 20. As shown, intermediate shaft 136 may include a cable tube that includes a plurality of wires 170 spun axially around a desired diameter. Each individual wire may be formed from a number of spun fibers. The cable tube structure may increases stiffness of intermediate shaft 136, which may help prevent structural deformation.

In some embodiments, the entire length of intermediate shaft 136 may be formed from or otherwise include a cable tube. In other embodiments, intermediate shaft 136 might be formed as a hybrid tube, with only a portion (e.g., a proximal portion) being formed as a cable tube. In these embodiments, at least a proximal section of the portion of intermediate shaft 136 including a cable tube may lie within handle 14, which may allow intermediate shaft 136 to provide structural support (e.g., resistance to bending, bowing, kinking, etc.) within handle 14. In some of these and in other embodiments, inner shaft 20 (and/or portions thereof) may be formed from cable tube.

The precise form of intermediate shaft 136 can vary. For example, the number of wires in the cable tube, the number of fibers in each of the wires, the diameter of the wires, the number of twists formed in the wires per unit length, the pitch of one or more of the wires, the material composition of the wires, or the like may vary. In addition, portions of the interior and/or exterior of the cable tube may include a coating. Moreover, the cable tube may also include an outer sleeve (not shown) and/or a surface. Furthermore, in embodiments where the cable tube extends along only a portion of intermediate shaft 136, the cable tube may be attached to intermediate shaft 136 in any suitable manner including, for example, welding, gluing, mechanically bonding, etc. These are just examples.

Figure 9:
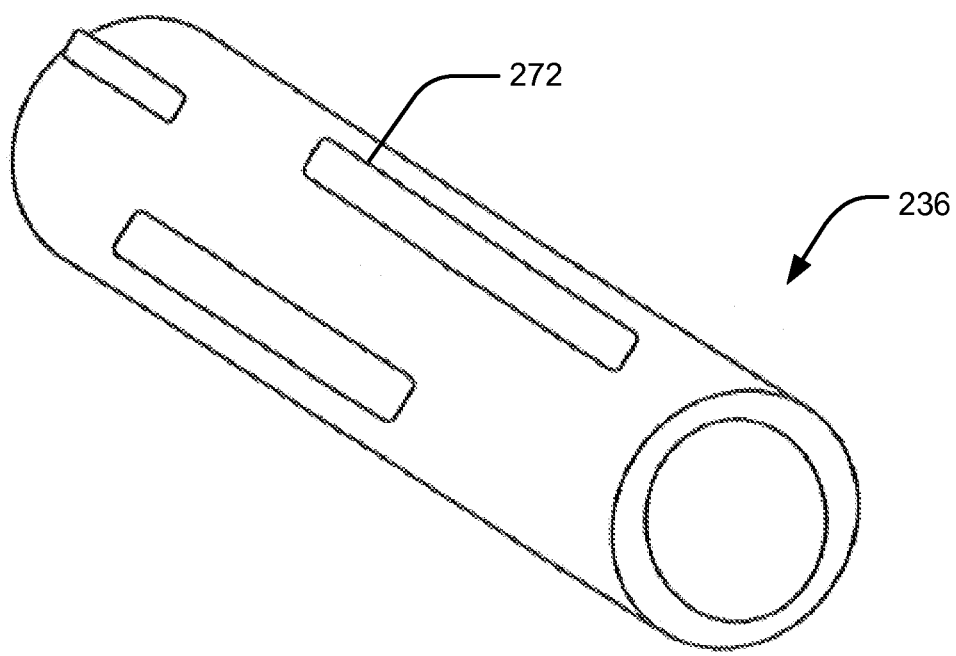
FIG. 9 is a side view of a portion of another example intermediate shaft.

Another example intermediate shaft 236 is shown in FIG. 9. In this example, intermediate shaft 236 (and/or portions thereof) may have a plurality of slots 272 formed therein. In some embodiments, slots 272 may be formed along essentially the entire length of intermediate shaft 236. In other embodiments, only a portion of intermediate shaft 236 may include slots 272. If multiple sections of intermediate shaft 236 are utilized (e.g., a first portion lacking slots 272 and a second portion including slots 272), the sections may be attached to one another in any suitable manner including, for example, welding, gluing, mechanically bonding, etc. In at least some embodiments, intermediate shaft 236 may be formed from a material that can provide structural support sufficient to resist bending, bowing, kinking, etc. However, slots 272 may provide an increase in flexibility, which may allow for increased trackability of intermediate shaft 236 (and/or systems like system 10 including intermediate shaft 236) through the vasculature.

Just like for intermediate shaft 136, numerous variations are contemplated for intermediate shaft 236. For example, the material composition may vary. In addition, intermediate shaft 236 may include an outer sleeve and/or surface finish. The length, location, pattern, shape, width, etc. of slots 272 may also vary. Some other examples of slot variations contemplated for slots 272 can be found in U.S. Provisional application Ser. No. 13/077,579, the entire disclosures of which are incorporated herein by reference.

Figure 10:
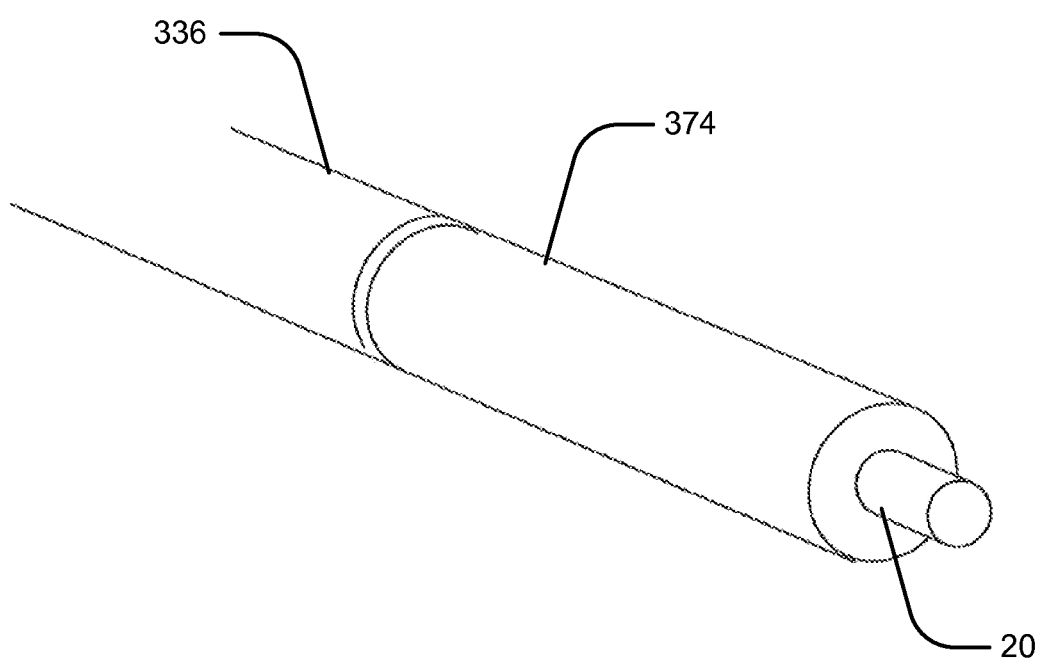
FIG. 10 is a side view of a portion of another example intermediate shaft and an example support member.

FIG. 10 illustrates another example intermediate shaft 336 and a support member 374. In general, support member 374 may provide resistance to bending, bowing, kinking, etc. of intermediate shaft 336 and/or inner shaft 20. In this example, support member 374 takes the form of a support sleeve that is positioned at the proximal end of the intermediate shaft 336. In some embodiments, support member 374 may take the form of a metallic tubular member that supports inner shaft 20 (and/or intermediate shaft 336). Just like the other supporting structures or members disclosed herein, support member 374 may vary. For example, the length, location, material composition, etc. of support member 374 may vary. Although the depicted embodiment of support sleeve 374 has a circular cross-section, a number of other designs could be employed. For example, the cross-section could exhibit a square cross-section or, indeed, any cross-section that would be convenient for manufacture or other factor. In some embodiments, support sleeve 374 may be attached to intermediate shaft 336 via an adhesive attachment means. Alternatively, other attachment methods may include thermal bonding, such as laser welding, melting, or ultrasonic welding. In other embodiments, support sleeve 374 may not be bonded to or otherwise attached to intermediate shaft 336.

Figure 11:
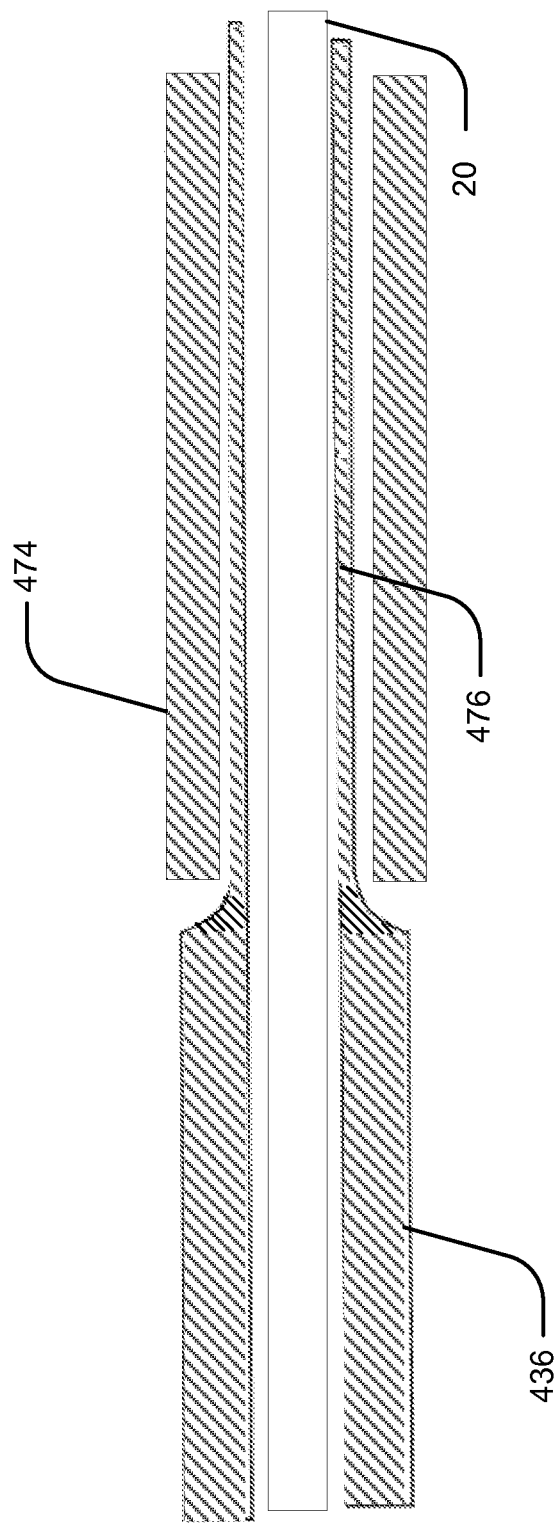
FIG. 11 is a side view of a portion of another example intermediate shaft and an example support member.

FIG. 11 illustrates another example intermediate shaft 436 and a support member 474. In this embodiment support member 474 may be fitted over necked-down region 476 of intermediate shaft 436, which may provide increased structural support to inner shaft 20. As discussed in relation to FIG. 10, various structural variations are contemplated for support member 474 (length, location, material composition, etc.). In addition, variations are also completed for the length of necked-down region 476, the amount that neck-down region 476 is reduced (e.g., the extent to which the outer diameter is reduced), the transition to the necked-down region 476, etc.

The materials that can be used for the various components of system 10 (and/or other systems disclosed herein) may include those commonly associated with medical devices. For simplicity purposes, the following discussion makes reference to shaft 12, deployment sheath 16, and inner member 20. However, this is not intended to limit the invention as the discussion may be applied to other similar members and/or components of members or systems disclosed herein.

Shaft 12, deployment sheath 16, and inner member 20, and/or other components of system 10 may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of shaft 12, deployment sheath 16, and inner member 20 may also be doped with, made of, or otherwise include a radiopaque material including those listed herein or other suitable radiopaque materials.

In some embodiments, a degree of MRI compatibility is imparted into system 10. For example, to enhance compatibility with Magnetic Resonance Imaging (MRI) machines, it may be desirable to make shaft 12, deployment sheath 16, and inner member 20, in a manner that would impart a degree of MRI compatibility. For example, shaft 12, deployment sheath 16, and inner member 20, or portions thereof, may be made of a material that does not substantially distort the image and create substantial artifacts (artifacts are gaps in the image). Certain ferromagnetic materials, for example, may not be suitable because they may create artifacts in an MRI image. Shaft 12, deployment sheath 16, and inner member 20, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be used to form shaft 12, deployment sheath 16, and inner member 20, and/or other components of system 10 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

In some embodiments, the exterior surface of the system 10 may include a coating, for example a lubricious, a hydrophilic, a protective, or other type of coating. Hydrophobic coatings such as fluoropolymers provide a dry lubricity which improves device handling and exchanges. Lubricious coatings improve steerability and improve lesion crossing capability. Suitable lubricious polymers may include silicone and the like, polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, the entire disclosures of which are incorporated herein by reference.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A stent delivery system, comprising:
   an inner shaft having a distal region;
   a stent disposed about the distal region;
   a single intermediate shaft disposed over the inner shaft and positioned proximally of the stent, a distal end of the intermediate shaft comprising a bumper that is disposed adjacent a proximal end of the stent, wherein the intermediate shaft includes a supported region having a reduced wall thickness, the supported region positioned at a proximal end of the intermediate shaft;
   a support member positioned along the supported region;
   a deployment sheath slidably disposed over the intermediate shaft and the support member, the deployment sheath comprising a proximal end and a distal end;
   a gear rack assembly attached to the proximal end of the deployment sheath with a clip, and a clip member is positioned within a groove of the gear rack assembly near the inner shaft and intermediate shaft such that the clip member can be associated therewith to fix a longitudinal position of the inner shaft and the intermediate shaft relative to the handle;
   a handle coupled to the deployment sheath; and
   wherein the proximal portion of the intermediate shaft is disposed within the handle.

2. The stent delivery system of claim 1, wherein only the supported region includes the support member.

3. The stent delivery system of claim 1, wherein the supported region extends distally from the handle.

4. The stent delivery system of claim 1, wherein the support member includes a cable tube.

5. The stent delivery system of claim 1, wherein the support member includes a slotted tubular member.

6. The stent delivery system of claim 1, wherein the support member includes a support sleeve.

7. The stent delivery system of claim 6, wherein the support member is disposed coaxially about the inner shaft and positioned adjacent to a proximal end of the intermediate shaft.

8. The stent delivery system of claim 1, wherein the inner shaft includes a second support member.

9. The stent delivery system of claim 8, wherein the second support member includes a cable tube.

10. The stent delivery system of claim 8, wherein the second support member includes a slotted tubular member.

11. A stent delivery system, comprising:
    an inner shaft having a distal region;
    a stent disposed about the distal region;
    a single intermediate shaft disposed over the inner shaft and positioned proximally of the stent, wherein a distal end of the intermediate shaft is disposed adjacent a proximal end of the stent, wherein the intermediate shaft comprises a supported portion with a reduced wall thickness, the supported portion being positioned adjacent to a proximal end of the intermediate shaft;
    a support member disposed along the supported portion of the intermediate shaft;
    a deployment sheath slidably disposed over the intermediate shaft, a distal end of the deployment sheath comprising a stepped portion, the stepped portion of the deployment sheath comprising a reinforcing member, the reinforcing member extending only along the stepped portion and extending at least along the stent, the reinforcing member is a braid, coil, or mesh;
    a handle coupled to the deployment sheath, the handle including a handle housing;
    a clip member disposed within the handle and configured to be secured along an interior surface of the handle, wherein the clip member allows a longitudinal position of the inner shaft and the intermediate shaft to be fixed relative to the handle;
    wherein the supported portion of the intermediate shaft extends under the deployment sheath and within the handle housing;

wherein the support member is configured to resist bowing of the intermediate shaft during proximal retraction of the deployment sheath; and an outer shaft disposed over the deployment sheath and positioned proximally of the stent.

12. The stent delivery system of claim 11, wherein the support member includes a cable tube.

13. The stent delivery system of claim 11, wherein the support member includes a slotted tubular member.

14. The stent delivery system of claim 11, wherein the support member of the intermediate shaft includes a support sleeve that is disposed coaxially about the inner shaft and positioned adjacent to a proximal end of the intermediate shaft.

15. The stent delivery system of claim 11, wherein the inner shaft includes a second support member.

16. The stent delivery system of claim 15, wherein the second support member includes a cable tube, a slotted tubular member, or both.

17. The stent delivery system of claim 11, wherein the reinforcing member of the stepped portion is embedded therein.

18. The stent delivery system of claim 11, wherein in the stepped portion of the deployment sheath, the thickness of a tubular wall of deployment sheath is not increased.

19. The stent delivery system of claim 11, wherein in the stepped portion of the deployment sheath, the thickness of a tubular wall of deployment sheath is increased.

20. A method for delivering a medical device, the method comprising:

advancing a stent delivery system through a body lumen to a position adjacent to an area of interest, the stent delivery system comprising:

an inner shaft having a distal region, a stent disposed about the distal region, a single intermediate shaft disposed over the inner shaft and positioned proximally of the stent, a distal end of the intermediate shaft comprising a bumper that is disposed adjacent a proximal end of the stent, wherein the intermediate shaft includes a supported region, the supported region positioned at a proximal end of the intermediate shaft, the intermediate shaft is formed as a hybrid tube with only the supported region of the proximal end of the intermediate shaft including a cable tube;

a support member positioned along the supported region;

a deployment sheath slidably disposed over the intermediate shaft and the support member a handle coupled to the deployment sheath, wherein at least the supported region of the proximal end of the intermediate shaft is disposed within the handle;

a clip member disposed within the handle and configured to be secured along an interior surface of the handle, wherein the clip member allows a longitudinal position of the inner shaft and the intermediate shaft to be fixed relative to the handle;

proximally retracting the deployment sheath; and wherein the support member resists bowing of the intermediate shaft during proximal retraction of the deployment sheath.

* * * * *